(12) United States Patent
Matusz

(10) Patent No.: US 8,921,586 B2
(45) Date of Patent: Dec. 30, 2014

(54) PROCESS FOR THE PRODUCTION OF AN OLEFIN OXIDE, A 1,2-DIOL, A 1,2-DIOL ETHER, A 1,2-CARBONATE, OR AN ALKANOLAMINE

(75) Inventor: Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 588 days.

(21) Appl. No.: 12/437,258

(22) Filed: May 7, 2009

(65) Prior Publication Data

US 2009/0281345 A1   Nov. 12, 2009

Related U.S. Application Data

(60) Provisional application No. 61/051,305, filed on May 7, 2008.

(51) Int. Cl.
C07D 301/10 (2006.01)

(52) U.S. Cl.
CPC ................................. *C07D 301/10* (2013.01)
USPC ......................................................... 549/536

(58) Field of Classification Search
USPC ......................................................... 549/536
See application file for complete search history.

(56) References Cited

U.S. PATENT DOCUMENTS

| | | | |
|---|---|---|---|
| 1,976,677 A | 10/1934 | Wittwer | 260/106 |
| 2,219,575 A | 10/1940 | McNamee | 260/348 |
| 3,893,910 A | 7/1975 | Robson | 208/138 |
| 3,950,507 A | 4/1976 | Kuklina et al. | 423/626 |
| 3,962,136 A | 6/1976 | Nielsen et al. | 252/454 |
| 4,007,135 A | 2/1977 | Hayden et al. | 252/467 |
| 4,010,115 A | 3/1977 | Nielsen et al. | 252/454 |
| 4,012,425 A | 3/1977 | Nielsen et al. | 260/348.5 R |
| 4,039,561 A | 8/1977 | Mitsuhata et al. | 260/348.34 |
| 4,097,414 A | 6/1978 | Cavitt | 252/476 |
| 4,102,820 A | 7/1978 | Cavitt | 252/463 |
| 4,206,128 A | 6/1980 | Cavitt | 260/348.34 |
| 4,212,772 A | 7/1980 | Mross et al. | 252/463 |
| 4,224,194 A | 9/1980 | Cavitt | 252/476 |
| 4,226,782 A | 10/1980 | Hayden et al. | 260/348.34 |
| 4,242,235 A | 12/1980 | Cognion et al. | 252/455 R |
| 4,321,206 A | 3/1982 | Cavitt | 260/348.34 |
| 4,356,312 A | 10/1982 | Nielsen et al. | 549/534 |
| 4,379,134 A | 4/1983 | Weber et al. | 423/626 |
| 4,389,338 A | 6/1983 | Mitsuhata et al. | 252/463 |
| 4,400,559 A | 8/1983 | Bhise | 568/858 |
| 4,410,453 A | 10/1983 | Kiovsky et al. | 502/253 |
| 4,419,222 A | 12/1983 | Grenoble et al. | 208/120 |
| 4,428,863 A | 1/1984 | Fry | 502/8 |
| 4,430,312 A | 2/1984 | Eickmeyer | 423/223 |
| 4,465,754 A | 8/1984 | Kuin et al. | 430/109 |
| 4,508,927 A | 4/1985 | Bhise et al. | 568/858 |
| 4,555,501 A | 11/1985 | Armstrong | 502/243 |
| 4,761,394 A | 8/1988 | Lauritzen | 502/348 |
| 4,766,105 A * | 8/1988 | Lauritzen | 502/216 |
| 4,808,738 A | 2/1989 | Lauritzen | 549/536 |
| 4,820,675 A | 4/1989 | Lauritzen | 502/216 |
| 4,822,900 A | 4/1989 | Hayden | 549/534 |
| 4,831,162 A | 5/1989 | Nakajima et al. | 549/534 |
| 4,845,296 A | 7/1989 | Ahmed et al. | 564/477 |
| 4,874,879 A | 10/1989 | Lauritzen et al. | 549/536 |
| 4,908,343 A | 3/1990 | Bhasin | 502/218 |
| 4,916,243 A | 4/1990 | Bhasin et al. | 549/534 |
| 4,939,114 A | 7/1990 | Nojiri et al. | 502/348 |
| 4,994,588 A | 2/1991 | Kapicak et al. | 549/534 |
| 5,012,027 A | 4/1991 | Abrevaya et al. | 585/443 |
| 5,051,395 A | 9/1991 | Mitchell et al. | 502/348 |
| 5,057,481 A | 10/1991 | Bhasin | 502/208 |
| 5,063,195 A | 11/1991 | Jin et al. | 502/341 |
| 5,100,859 A | 3/1992 | Gerdes et al. | 502/439 |
| 5,102,848 A | 4/1992 | Soo et al. | 502/218 |
| 5,106,802 A | 4/1992 | Horiuchi et al. | 502/65 |
| 5,112,795 A | 5/1992 | Minahan et al. | 502/324 |
| 5,145,658 A | 9/1992 | Chao | 423/232 |
| 5,155,242 A | 10/1992 | Shankar et al. | 549/534 |
| 5,187,140 A | 2/1993 | Thorsteinson et al. | 502/348 |
| 5,374,738 A | 12/1994 | Boen et al. | 548/207 |
| 5,380,697 A | 1/1995 | Matusz et al. | 502/348 |
| 5,380,885 A | 1/1995 | Kemp | 549/536 |

(Continued)

FOREIGN PATENT DOCUMENTS

| | | | | |
|---|---|---|---|---|
| CA | 1180538 | 1/1985 | | 23/356 |
| CN | 1080636 | 1/1994 | | C07D 301/10 |

(Continued)

OTHER PUBLICATIONS

Kirk-Othmer's Encyclopedia of Chemical, $3^{rd}$ edition, vol. 9, 1980 pp. 445-447.

(Continued)

*Primary Examiner* — Joseph Kosack

(57) ABSTRACT

A process for the epoxidation of an olefin comprising contacting a reactor feed comprising an olefin, oxygen, and carbon dioxide, with a catalyst comprising a carrier and, deposited on the carrier, silver, a rhenium promoter, and a potassium promoter; wherein the carbon dioxide is present in the reactor feed in a quantity of at most 3 mole percent based on the total epoxidation reactor feed;

the potassium promoter is deposited on the carrier in a quantity of at least 0.5 mmole/kg, relative to the weight of the catalyst; and the carrier contains water leachable potassium in a quantity of less than 55 parts per million by weight, relative to the weight of the carrier;

a process for preparing a 1,2-diol, a 1,2-diol ether, a 1,2-carbonate, or an alkanolamine.

21 Claims, No Drawings

(56) References Cited

U.S. PATENT DOCUMENTS

| | | | |
|---|---|---|---|
| 5,395,812 A | 3/1995 | Nagase et al. | 502/238 |
| 5,407,888 A | 4/1995 | Herzog et al. | 502/317 |
| 5,418,202 A | 5/1995 | Evans et al. | 502/348 |
| 5,428,202 A | 6/1995 | Rossi | 219/110 |
| 5,444,034 A | 8/1995 | Rizkalla | 502/347 |
| 5,504,052 A | 4/1996 | Rizkalla et al. | 502/347 |
| 5,504,053 A | 4/1996 | Chou et al. | 502/348 |
| 5,597,773 A | 1/1997 | Evans et al. | 502/348 |
| 5,646,087 A | 7/1997 | Rizkalla et al. | 502/347 |
| 5,703,253 A | 12/1997 | Evans et al. | 549/536 |
| 5,705,661 A | 1/1998 | Iwakura et al. | 549/536 |
| 5,736,483 A | 4/1998 | Rizkalla | 502/347 |
| 5,739,075 A | 4/1998 | Matusz | 502/302 |
| 5,770,746 A | 6/1998 | Cooker et al. | 549/534 |
| 5,780,656 A | 7/1998 | Rizkalla et al. | 549/534 |
| 5,801,259 A | 9/1998 | Kowaleski | 549/536 |
| 5,840,932 A | 11/1998 | Evans et al. | 549/512 |
| 5,854,167 A | 12/1998 | Rizkalla et al. | 502/216 |
| 5,856,534 A | 1/1999 | Cooker et al. | 549/534 |
| 5,929,259 A | 7/1999 | Lockemeyer | 549/534 |
| 5,965,481 A | 10/1999 | Durand et al. | 502/304 |
| 6,040,467 A | 3/2000 | Papavassiliou et al. | 549/534 |
| 6,080,897 A | 6/2000 | Kawabe | 568/858 |
| 6,087,299 A | 7/2000 | Grub et al. | 502/347 |
| 6,251,820 B1 | 6/2001 | Tsuji | 502/242 |
| 6,368,998 B1 | 4/2002 | Kockemeyer | 502/347 |
| 6,372,925 B1 | 4/2002 | Evans et al. | 549/536 |
| 6,452,027 B1 | 9/2002 | Billig et al. | 549/538 |
| 6,498,122 B2 | 12/2002 | Nakashiro | 502/347 |
| 6,498,259 B1 | 12/2002 | Grey et al. | 549/533 |
| 6,504,053 B1 | 1/2003 | Chaturvedi et al. | 562/549 |
| 6,511,938 B1 | 1/2003 | Liu et al. | 502/347 |
| 6,533,843 B2 | 3/2003 | Billig et al. | 95/172 |
| 6,534,441 B1 | 3/2003 | Bartley et al. | 502/337 |
| 6,579,825 B2 | 6/2003 | Lockemeyer | 502/347 |
| 6,600,056 B1 | 7/2003 | Mikawa et al. | 549/534 |
| 6,656,874 B2 | 12/2003 | Lockemeyer | 502/347 |
| 6,750,173 B2 | 6/2004 | Rizkalla et al. | 502/348 |
| 6,762,311 B2 | 7/2004 | Rizkalla et al. | 549/534 |
| 6,908,879 B1 | 6/2005 | Shima et al. | 502/242 |
| 7,102,022 B2 | 9/2006 | Evans et al. | 549/536 |
| 2002/0010094 A1 | 1/2002 | Lockemeyer | 502/439 |
| 2003/0162984 A1 | 8/2003 | Lockemeyer et al. | 549/534 |
| 2003/0191019 A1 | 10/2003 | Rizkalla et al. | 502/243 |
| 2004/0049061 A1 | 3/2004 | Lockemeyer et al. | 549/536 |
| 2004/0110971 A1 | 6/2004 | Evans et al. | 549/534 |
| 2004/0110973 A1 | 6/2004 | Matusz | 549/534 |
| 2004/0198992 A1 | 10/2004 | Matusz et al. | 549/533 |
| 2005/0222442 A1 | 10/2005 | Lockemeyer | 549/534 |
| 2007/0185339 A1 | 8/2007 | Lu | 549/534 |
| 2007/0225511 A1 | 9/2007 | Bortinger et al. | 549/536 |

FOREIGN PATENT DOCUMENTS

| | | | |
|---|---|---|---|
| CN | 1802363 | 7/2006 | C07D 301/10 |
| EP | 3642 | 8/1979 | C07D 301/10 |
| EP | 0026605 | 4/1981 | E04C 2/34 |
| EP | 0161930 | 11/1985 | C07D 301/10 |
| EP | 0211521 | 2/1987 | B01J 23/66 |
| EP | 266015 | 5/1988 | B01J 23/68 |
| EP | 0326392 | 8/1989 | C07D 301/10 |
| EP | 0327356 | 8/1989 | C07D 301/10 |
| EP | 0352849 | 1/1990 | C07D 301/10 |
| EP | 0352850 | 1/1990 | C07D 301/10 |
| EP | 0176253 | 3/1990 | C07D 301/10 |
| EP | 0226234 | 8/1990 | B01J 3/16 |
| EP | 0393785 | 10/1990 | C07D 301/10 |
| EP | 0448157 | 3/1991 | C07C 31/20 |
| EP | 0480537 | 4/1992 | B01J 23/66 |
| EP | 0480539 | 4/1992 | C07D 301/10 |
| EP | 0496470 | 7/1992 | C07D 301/10 |
| EP | 0557833 | 9/1993 | B01J 23/50 |
| EP | 0567273 | 10/1993 | C07D 301/10 |
| EP | 0716884 | 6/1996 | B01J 23/66 |
| EP | 0425020 | 2/1999 | C07D 301/10 |
| EP | 0933130 | 8/1999 | B01J 23/66 |
| EP | 1002575 | 3/2005 | B01J 23/04 |
| EP | 1532125 | 5/2005 | |
| GB | 117663 | 7/1918 | |
| GB | 119183 | 9/1918 | |
| GB | 1489335 | 10/1974 | B01J 23/66 |
| GB | 1594362 | 7/1981 | B01J 23/66 |
| GB | 2161480 | 6/1984 | C07D 301/10 |
| JP | 63126552 | 5/1963 | B01J 23/68 |
| JP | 50095213 | 7/1975 | C07D 301/10 |
| JP | 56105750 | 8/1981 | B01J 23/66 |
| JP | 3068449 | 3/1991 | B01J 23/66 |
| JP | 4346835 | 12/1992 | B01J 23/66 |
| RU | 2045335 | 10/1995 | B01J 23/66 |
| SU | 1255200 | 3/1982 | B01J 23/96 |
| WO | WO9505896 | 3/1995 | B01J 23/66 |
| WO | WO9507139 | 3/1995 | B01J 23/66 |
| WO | WO9517957 | 7/1995 | B01J 23/68 |
| WO | WO9604989 | 2/1996 | B01J 23/50 |
| WO | WO9623585 | 8/1996 | B01J 23/66 |
| WO | WO96235286 | 8/1996 | B01J 37/00 |
| WO | WO9746317 | 12/1997 | B01J 23/66 |
| WO | WO9845280 | 10/1998 | C07D 301/10 |
| WO | WO9858920 | 12/1998 | C07D 301/10 |
| WO | WO9952883 | 10/1999 | C07D 301/04 |
| WO | WO0015332 | 3/2000 | B01J 23/04 |
| WO | WO0015333 | 3/2000 | B01J 23/50 |
| WO | WO0015334 | 3/2000 | B01J 23/50 |
| WO | WO0015335 | 3/2000 | B01J 23/50 |
| WO | WO0196324 | 12/2001 | C07D 301/00 |
| WO | WO03072246 | 9/2003 | B01J 23/66 |
| WO | WO2004002917 | 1/2004 | C04B 23/66 |
| WO | WO2004002954 | 1/2004 | |
| WO | WO2004002971 | 1/2004 | C07D 301/10 |
| WO | WO2004002972 | 1/2004 | C07D 301/10 |
| WO | WO2005035513 | 8/2004 | C07D 301/10 |
| WO | WO 2004/078737 | * 9/2004 | C07D 301/10 |
| WO | WO2004078736 | 9/2004 | C07D 301/10 |
| WO | WO2004078737 | 9/2004 | C07D 301/10 |
| WO | WO2004089539 | 10/2004 | B01J 23/68 |
| WO | WO2004092148 | 10/2004 | C07D 301/10 |
| WO | WO2004101141 | 11/2004 | B01J 19/30 |
| WO | WO2005097318 | 10/2005 | B01J 23/68 |
| WO | WO2006020718 | 2/2006 | B01J 23/50 |
| WO | WO2006028940 | 3/2006 | B01J 21/04 |
| WO | WO2006102189 | 9/2006 | B01J 8/06 |
| WO | WO2007095453 | 8/2007 | B01J 21/04 |
| WO | WO2007122090 | 11/2007 | |

OTHER PUBLICATIONS

Brunauer, Stephen, Emmett, P.H. and Teller, Edward: "Adsorption of Gases in Multimolecular Layers", Journal of the American Chemical Society, Feb. 1938, pp. 309-316.

J. M. Kobe et al., Encyclopedia of Catalysis, vol. 3, l'T. Korrath (Ed.), published Dec. 2002, pp. 246-264.

Intercom Article, Workshop on Safety at SNR—Forum: 100 Years Shell Pernis (English translation provided), Apr. 2002.

Robert H. Perry, et al., Perry's Chemical Engineers Handbook, 6$^{th}$ Ed., pp. 14-20 to 20-51 (1984).

Beilstein Institute for Organic Chemistry, Frankfurt-Main, DE XP002296657, J. Am. Chem. Society, vol. 56, (1934) pp. 1870-1872.

* cited by examiner

PROCESS FOR THE PRODUCTION OF AN OLEFIN OXIDE, A 1,2-DIOL, A 1,2-DIOL ETHER, A 1,2-CARBONATE, OR AN ALKANOLAMINE

This application claims the benefit of U.S. Provisional Application No. 61/051,305 filed May 7, 2008.

FIELD OF THE INVENTION

The present invention relates to a process for the production of an olefin oxide, a 1,2-diol, a 1,2-diol ether, a 1,2-carbonate, or an alkanolamine.

BACKGROUND OF THE INVENTION

In olefin epoxidation, a reactor feed containing an olefin and oxygen is contacted with a catalyst under epoxidation conditions. The olefin is reacted with oxygen to form an olefin oxide. A product mix results that contains olefin oxide and, typically, unreacted reactor feed and combustion products.

Carbon dioxide is a by-product in the epoxidation process, and may be present in the reactor feed. Under commercial operation of epoxidation processes, the epoxidation reactor feed is formed by adding fresh oxygen and olefin to a recycle gas stream which comprises, besides unreacted and recycled oxygen and olefin, quantities of carbon dioxide, water, and other gases.

The olefin oxide may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine.

The catalytic epoxidation of olefins using a silver-based catalyst has been known for a long time. Conventional silver-based epoxidation catalysts have provided the olefin oxides notoriously in a low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximum selectivity of this reaction, based on the stoichiometry of the reaction equation

cf. Kirk-Othmer's *Encyclopedia of Chemical Technology*, 3$^{rd}$ ed., vol. 9, 1980, p. 445.

Modern silver-based catalysts however are more selective towards olefin oxide production. When using the modern catalysts in the epoxidation of ethylene, the selectivity towards ethylene oxide can reach values above the 6/7 or 85.7 mole-% limit referred to. Such highly selective epoxidation catalysts are known from U.S. Pat. No. 4,766,105 and U.S. Pat. No. 4,761,394. However, the highly selective epoxidation catalysts employ higher reaction temperatures than do the conventional epoxidation catalysts for a given ethylene oxide yield, and they exhibit a greater rate of catalyst deactivation than conventional epoxidation catalysts.

The selectivity is the fraction of the converted olefin yielding the desired olefin oxide. As the catalyst ages, the fraction of the olefin converted normally decreases with time and to maintain a constant level of olefin oxide production the temperature of the reaction may be increased.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity over long periods yield substantial dividends in terms of process efficiency.

International Patent Application WO 2004/078737 discusses the improvement in performance of highly selective epoxidation catalysts during the production of ethylene oxide when the reactor feed contains less than 2 mole-% of carbon dioxide, relative to the total reactor feed.

It is desirable to find a way to further improve the epoxidation process, for example improving the selectivity of a highly selective epoxidation catalyst in the manufacture of olefin oxide while also improving the stability of such catalyst.

SUMMARY OF THE INVENTION

The present invention provides a process for the epoxidation of an olefin comprising contacting a reactor feed comprising an olefin, oxygen, and carbon dioxide, with a catalyst comprising a carrier and, deposited on the carrier, silver, a rhenium promoter, and a potassium promoter; wherein
the carbon dioxide is present in the reactor feed in a quantity of less than 2 mole percent based on the total epoxidation reactor feed;
the potassium promoter is deposited on the carrier in a quantity of at least 0.5 mmole/kg, relative to the weight of the catalyst; and
the carrier contains water leachable potassium in a quantity of less than 55 parts per million by weight, relative to the weight of the carrier.

The invention also provides a process for preparing a 1,2-diol, a 1,2-diol ether, a 1,2-carbonate, or an alkanolamine comprising obtaining an olefin oxide by the process for the epoxidation of an olefin according to the present invention, and converting the olefin oxide into the 1,2-diol, the 1,2-diol ether, the 1,2-carbonate, or the alkanolamine.

DETAILED DESCRIPTION OF THE INVENTION

It has unexpectedly been found that depositing silver, a potassium promoter, and a rhenium promoter, on a carrier having low amounts of water leachable potassium can result in a catalyst that demonstrates an unexpected improvement in initial selectivity, stability and other benefits when operated under low carbon dioxide conditions.

Generally, the epoxidation catalyst is a supported catalyst. The carrier may be selected from a wide range of materials. Such carrier materials may be natural or artificial inorganic materials and they include silicon carbide and alkaline earth metal carbonates, such as calcium carbonate. Preferred are refractory carrier materials, such as alumina, magnesia, zirconia, silica, and mixtures thereof. The most preferred carrier material is α-alumina.

The carriers may be fluoride-mineralized carriers or non-fluoride-mineralized carriers. Fluoride-mineralized carriers are obtained by combining alpha-alumina or alpha-alumina precursor(s) with a fluorine-containing species that is capable of liberating fluoride when the combination is calcined, and calcining the combination. The manner by which the fluorine-containing species is introduced into the carrier is not limited, and those methods known in the art for incorporating a fluorine-containing species into a carrier (and those fluoride-mineralized carriers obtained therefrom) may be used for the present invention. For example, U.S. Pat. No. 3,950,507 and U.S. Pat. No. 4,379,134 disclose methods for making fluoride-mineralized carriers and are hereby incorporated by reference.

The carriers may be lamellar or platelet-type carriers or non-lamellar or non-platelet-type carriers. Lamellar or platelet-type carriers contain a particulate matrix having a morphology characterizable as lamellar or platelet-type, which terms are used interchangeably. Lamellar or platelet-type carriers contain particles which have in at least one direction a size greater than 0.1 micrometers and have at least one substantially flat major surface. Such particles may have two or more flat major surfaces.

The surface area of the carrier may suitably be at least 0.1 $m^2/g$, preferably at least 0.3 $m^2/g$, more preferably at least 0.5 $m^2/g$, and in particular at least 0.6 $m^2/g$, relative to the weight of the carrier; and the surface area may suitably be at most 20 $m^2/g$, preferably at most 10 $m^2/g$, more preferably at most 6 $m^2/g$, and in particular at most 4 $m^2/g$, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carriers, in particular when they are alpha alumina carriers optionally comprising in addition silica, alkali metal and/or alkaline earth metal components, provide improved performance and stability of operation.

The water absorption of the carrier may suitably be at least 0.2 g/g, preferably at least 0.25 g/g, more preferably at least 0.3 g/g, most preferably at least 0.35 g/g; and the water absorption may suitably be at most 0.85 g/g, preferably at most 0.7 g/g, more preferably at most 0.65 g/g, most preferably at most 0.6 g/g. The water absorption of the carrier may be in the range of from 0.2 to 0.85 g/g, preferably in the range of from 0.25 to 0.7 g/g, more preferably from 0.3 to 0.65 g/g, most preferably from 0.3 to 0.6 g/g. A higher water absorption may be in favor in view of a more efficient deposition of the metal and promoters on the carrier by impregnation. However, at a higher water absorption, the carrier, or the catalyst made therefrom, may have lower crush strength. As used herein, water absorption is deemed to have been measured in accordance with ASTM C20, and water absorption is expressed as the weight of the water that can be absorbed into the pores of the carrier, relative to the weight of the carrier.

The carrier has a quantity of water leachable potassium of less than 55 parts per million by weight (ppmw), relative to the weight of the carrier. Preferably, the carrier has a quantity of water leachable potassium of at most 50 ppmw, more preferably at most 45 ppmw, most preferably less than 39 ppmw, in particular at most 35 ppmw, same basis. The quantity of water leachable potassium in the carrier is deemed to be the quantity insofar as it can be extracted from the carrier. The extraction involves extracting a 2-gram sample of the carrier three times by heating it in 25-gram portions of de-ionized water for 5 minutes at 100° C. and determining in the combined extracts the amount of alkali metal by using a known method, for example atomic absorption spectroscopy.

A carrier may be washed, to remove soluble residues, before deposition of the catalyst ingredients on the carrier. Additionally, the materials used to form the carrier, including the burnout materials, may be washed to remove soluble residues. Such carriers are described in U.S. Pat. No. 6,368,998 and WO-A2-2007/095453, which are incorporated herein by reference. On the other hand, unwashed carriers having such low quantities of water leachable potassium may also be used successfully. Washing of the carrier generally occurs under conditions effective to remove most of the soluble and/or ionizable materials from the carrier.

The washing liquid may be, for example water, aqueous solutions comprising one or more salts, or aqueous organic diluents. Suitable salts for inclusion in an aqueous solution may include, for example ammonium salts. Suitable ammonium salts may include, for example ammonium nitrate, ammonium oxalate, ammonium fluoride, and ammonium carboxylates, such as ammonium acetate, ammonium citrate, ammonium hydrogencitrate, ammonium formate, ammonium lactate, and ammonium tartrate. Suitable salts may also include other types of nitrates such as alkali metal nitrates, for example lithium nitrate, potassium nitrate and cesium nitrate. Suitable quantities of total salt present in the aqueous solution may be at least 0.001% w, in particular at least 0.005% w, more in particular at least 0.01% w and at most 10% w, in particular at most 1% w, for example 0.03% w. Suitable organic diluents which may or may not be included are, for example, one or more of methanol, ethanol, propanol, isopropanol, tetrahydrofuran, ethylene glycol, ethylene glycol dimethyl ether, diethylene glycol dimethyl ether, dimethylformamide, acetone, or methyl ethyl ketone.

The preparation of the silver catalyst is known in the art and the known methods are applicable to the preparation of the catalyst which may be used in the practice of the present invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697, U.S. Pat. No. 5,739,075, U.S. Pat. No. 4,766,105, and U.S. Pat. No. 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 190 g/kg, or 250 g/kg, or 350 g/kg. As used herein, unless otherwise specified, the weight of the catalyst is deemed to be the total weight of the catalyst including the weight of the carrier and catalytic components.

The catalyst for use in the present invention additionally comprises a rhenium promoter component. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The rhenium promoter may be present in a quantity of at least 0.01 mmole/kg, preferably at least 0.1 mmole/kg, more preferably at least 0.5 mmole/kg, most preferably at least 1 mmole/kg, in particular at least 1.25 mmole/kg, more in particular at least 1.5 mmole/kg, calculated as the total quantity of the element relative to the weight of the catalyst. The rhenium promoter may be present in a quantity of at most 500 mmole/kg, preferably at most 50 mmole/kg, more preferably at most 10 mmole/kg, calculated as the total quantity of the element relative to the weight of the catalyst.

The catalyst further comprises a potassium promoter deposited on the carrier. The potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with the present invention can exhibit an improvement in selectivity, activity, and/or stability of the catalyst especially when operated under conditions where the reaction feed contains low levels of carbon dioxide.

In an embodiment, the catalyst may preferably contain a quantity of potassium such that the amount of water extractable potassium of the catalyst may be at least 1.25 mmole/kg, relative to the weight of the catalyst, suitably at least 1.5 mmole/kg, more suitably at least 1.75 mmole/kg, same basis. Suitably, the catalyst may contain water extractable potassium in a quantity of at most 10 mmole/kg, more suitably at most 7.5 mmole/kg, most suitably at most 5 mmole/kg, same basis. Suitably, the catalyst may contain water extractable potassium in a quantity in the range of from 1.25 to 10 mmole/kg, more suitably from 1.5 to 7.5 mmole/kg, most suitably from 1.75 to 5 mmole/kg, same basis. The source of water extractable potassium may originate from the carrier and/or the catalytic components. The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

The catalyst for use in the present invention may additionally comprise a rhenium co-promoter. The rhenium co-promoter may be selected from tungsten, molybdenum, chromium, sulfur, phosphorus, boron, and mixtures thereof.

The rhenium co-promoter may be present in a total quantity of at least 0.1 mmole/kg, more typically at least 0.25 mmole/kg, and preferably at least 0.5 mmole/kg, calculated as the element (i.e. the total of tungsten, chromium, molybdenum, sulfur, phosphorus and/or boron), relative to the weight of the catalyst. The rhenium co-promoter may be present in a total quantity of at most 40 mmole/kg, preferably at most 10 mmole/kg, more preferably at most 5 mmole/kg, on the same basis. The form in which the rhenium co-promoter may be deposited on the carrier is not material to the invention. For example, it may suitably be provided as an oxide or as an oxyanion, for example, as a sulfate, borate or molybdate, in salt or acid form.

In an embodiment, the catalyst comprises the rhenium promoter and additionally a first co-promoter component and a second co-promoter component. The first co-promoter may be selected from sulfur, phosphorus, boron, and mixtures thereof. It is particularly preferred that the first co-promoter comprises, as an element, sulfur. The second co-promoter component may be selected from tungsten, molybdenum, chromium, and mixtures thereof. It is particularly preferred that the second co-promoter component comprises, as an element, tungsten and/or molybdenum, in particular tungsten. The form in which the first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

In this embodiment, the first co-promoter may be present in a total quantity of at least 0.2 mmole/kg, preferably at least 0.3 mmole/kg, more preferably at least 0.5 mmole/kg, most preferably at least 1 mmole/kg, in particular at least 1.5 mmole/kg, more in particular at least 2 mmole/kg, calculated as the total quantity of the element (i.e., the total of sulfur, phosphorus, and/or boron) relative to the weight of the catalyst. The first co-promoter may be present in a total quantity of at most 50 mmole/kg, preferably at most 40 mmole/kg, more preferably at most 30 mmole/kg, most preferably at most 20 mmole/kg, in particular at most 10 mmole/kg, more in particular at most 6 mmole/kg, calculated as the total quantity of the element relative to the weight of the catalyst.

In this embodiment, the second co-promoter component may be present in a total quantity of at least 0.1 mmole/kg, preferably at least 0.15 mmole/kg, more preferably at least 0.2 mmole/kg, most preferably at least 0.25 mmole/kg, in particular at least 0.3 mmole/kg, more in particular at least 0.4 mmole/kg, calculated as the total quantity of the element (i.e., the total of tungsten, molybdenum, and/or chromium) relative to the weight of the catalyst. The second co-promoter may be present in a total quantity of at most 40 mmole/kg, preferably at most 20 mmole/kg, more preferably at most 10 mmole/kg, most preferably at most 5 mmole/kg, calculated as the total quantity of the element relative to the weight of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

In an embodiment, the catalyst comprises the rhenium promoter in a quantity of greater than 1 mmole/kg, relative to the weight of the catalyst, and the total quantity of the first co-promoter and the second co-promoter deposited on the carrier may be at most 3.8 mmole/kg, calculated as the total quantity of the elements (i.e., the total of sulfur, phosphorous, boron, tungsten, molybdenum and/or chromium) relative to the weight of the catalyst. In this embodiment, the total quantity of the first co-promoter and the second co-promoter may preferably be at most 3.5 mmole/kg, more preferably at most 3 mmole/kg of catalyst. In this embodiment, the total quantity of the first co-promoter and the second co-promoter may preferably be at least 0.1 mmole/kg, more preferably at least 0.5 mmole/kg, most preferably at least 1 mmole/kg of the catalyst.

The catalyst may preferably further comprise a further element deposited on the carrier. Eligible further elements may be one or more of nitrogen, fluorine, alkali metals, alkaline earth metals, titanium, hafnium, zirconium, vanadium, thallium, thorium, tantalum, niobium, gallium and germanium and mixtures thereof. Preferably, the alkali metals are selected from lithium, sodium and/or cesium. Preferably, the alkaline earth metals are selected from calcium, magnesium and barium. Preferably, the further element may be present in the catalyst in a total quantity of from 0.01 to 500 mmole/kg, more preferably from 0.5 to 100 mmole/kg, calculated as the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

As used herein, unless otherwise specified, the quantity of alkali metal present in the catalyst or carrier is deemed to be the quantity insofar as it can be extracted from the catalyst or carrier. The extraction involves extracting a 2-gram sample of the catalyst or carrier three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Although the present epoxidation process may be carried out in many ways, it is preferred to carry it out as a gas phase process, i.e. a process in which the reactor feed is contacted in the gas phase with the catalyst which is present as a solid material, typically in a packed bed. Generally the process is carried out as a continuous process.

The reactor feed of the inventive process comprises an olefin, oxygen and a quantity of carbon dioxide. The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the reactor feed may be selected within a wide range. Typically, the quantity of the olefin present in the reactor feed will be at most 80 mole percent, relative to the total reactor feed. Preferably, it will be in the range of from 0.5 to 70 mole percent, in particular from 1 to 60 mole percent, on the same basis. As used herein, the reactor feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole percent) or very high purity (at least 99.5 mole percent) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the reactor feed may be selected within a wide range. However, in practice, oxygen is generally applied in a quantity which avoids the flammable regime. Typically, the quantity of oxygen applied will be within the range of from 1 to 15 mole percent, more typically from 2 to 12 mole percent of the total reactor feed.

In order to remain outside the flammable regime, the quantity of oxygen present in the reactor feed may be lowered as the quantity of the olefin is increased. The actual safe operating ranges depend, along with the reactor feed composition, also on the reaction conditions such as the reaction temperature and the pressure.

An advantage of the present invention is that, when the epoxidation process is conducted in the presence of a catalyst containing silver, a rhenium promoter, and a potassium promoter under process conditions such that the reactor feed contains low levels of carbon dioxide, an unexpected improvement in catalyst performance can be observed, in particular initial selectivity, stability and other benefits. In an olefin oxide process a typical epoxidation reactor feed generally comprises a quantity of carbon dioxide exceeding 4 mole percent, relative to the total reactor feed. The process of the present invention is conducted under conditions where the quantity of carbon dioxide in the reactor feed is less than 2 mole percent, preferably less than 1.5 mole percent, more preferably less than 1.2 mole percent, most preferably less than 1 mole percent, in particular at most 0.75 mole percent, relative to the total reactor feed. In the normal practice of the present invention, the quantity of carbon dioxide present in the reactor feed is at least 0.1 mole percent, or at least 0.2 mole percent, or at least 0.3 mole percent, relative to the total reactor feed.

A reaction modifier may be present in the reactor feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride.

Suitable nitrogen oxides are of the general formula $NO_x$ wherein x is in the range of from 1 to 2.5, and include for example NO, $N_2O_3$, $N_2O_4$, and $N_2O_5$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the reactor feed, for example up to 0.1 mole percent, relative to the total reactor feed, for example from $0.01 \times 10^{-4}$ to 0.01 mole percent. In particular when the olefin is ethylene, it is preferred that the reaction modifier is present in the reactor feed in a quantity of from $0.1 \times 10^{-4}$ to $500 \times 10^{-4}$ mole percent, in particular from $0.2 \times 10^{-4}$ to $200 \times 10^{-4}$ mole percent, relative to the total reactor feed.

In addition to the olefin and oxygen, the reactor feed may contain one or more additional components, such as inert gases and saturated hydrocarbons. Inert gases, for example nitrogen or argon, may be present in the reactor feed in a quantity of from 30 to 90 mole percent, typically from 40 to 80 mole percent. Suitable saturated hydrocarbons are methane and ethane. If saturated hydrocarbons are present, they may be present in a quantity of up to 80 mole percent, relative to the total reactor feed, in particular up to 75 mole percent. Frequently they are present in a quantity of at least 30 mole percent, more frequently at least 40 mole percent. Saturated hydrocarbons may be added to the reactor feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l.h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. As used herein, the activity is a measurement of the temperature required to achieve a particular ethylene oxide production level. The lower the temperature, the better the activity. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

The olefin oxide produced in the epoxidation process may be converted into a 1,2-diol, a 1,2-diol ether, a 1,2-carbonate, or an alkanolamine. As the present invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. The alkanolamine may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Preparation of Stock Silver Solution

This example describes the preparation of a stock silver impregnation solution used in preparing Catalyst A in Example 2.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh de-ionized water equal to the amount removed was added back to the silver solution. The solution was stirred for 15 minutes at 40° C. The process was repeated until the conductivity of the water removed was less than 90 μmho/cm. 1500 ml fresh de-ionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time. Water was removed from this mixture to leave a highly concentrated silver-containing slurry. The silver oxalate slurry was cooled to 30° C.

699 g of 92 weight percent ethylenediamine (8% de-ionized water) was added while maintaining a temperature no greater than 30° C. The final solution was used as a stock silver impregnation solution for preparing Catalyst A.

Example 2

Preparation of Catalysts

Catalyst A:

Catalyst A was prepared by the following procedure: To 204 grams of stock silver solution of specific gravity 1.558 g/ml was added 0.1779 g of ammonium perrhenate in 2 g of 1:1 ethylenediamine/water; 0.0491 g of ammonium metatungstate dissolved in 2 g of 1:1 ammonia/water; 0.1273 g of lithium sulfate monohydrate dissolved in 2 g of water; and 0.2087 g of lithium hydroxide monohydrate dissolved in 2 g of water, 0.067 g of potassium nitrate dissolved in 2 g of water. Additional water was added to adjust the specific gravity of the solution to 1.504 g/ml. 50 g of the resulting solution was mixed with 0.1071 g of 50% w cesium hydroxide solution, producing the final impregnation solution. A vessel containing 30 grams of Carrier A hollow cylinders, see Table I below, was evacuated to 20 mm Hg for 1 minute and the final impregnation solution was added to Carrier A while under vacuum, then the vacuum was released and the carrier allowed to contact the liquid for 3 minutes. The impregnated Carrier A was then centrifuged at 500 rpm for 2 minutes to remove excess liquid. Impregnated Carrier A was placed in a vibrating shaker and dried in air flowing at a rate of 16.2 Nl/h at 250° C. for 7 minutes producing Catalyst A.

The final composition of Catalyst A comprised the following, calculated on the basis of pore volume impregnation: 17.2% w silver; 2 mmole Re/kg; 0.6 mmole W/kg; 3 mmole S/kg; 21 mmole Li/kg; 2 mmole K/kg; and 4.4 mmole Cs/kg. These values are relative to the weight of the catalyst.

The quantity of water extractable potassium present in the catalyst was measured by heating it in 25-gram portions of de-ionized water for 5 minutes at 100° C. and determining in the combined extracts the amount of potassium by using atomic absorption spectroscopy. Catalyst A contained water extractable potassium in a quantity of 97 ppmw, relative to the weight of the catalyst (i.e., 2.5 mmoles/kg).

Catalyst B:

Catalyst B was prepared in a similar manner as Catalyst A having a final composition of the following, calculated on the basis of pore volume impregnation: 17.2% w silver; 2 mmole Re/kg; 0.6 mmole W/kg; 3 mmole S/kg; 21 mmole Li/kg; and 6 mmole Cs/kg. These values are relative to the weight of the catalyst.

The quantity of water extractable potassium present in Catalyst B was also measured by the method discussed above. Catalyst B contained water extractable potassium in a quantity of 35 ppmw, relative to the weight of the catalyst (i.e., <1 mmole/kg).

TABLE I

| Carrier A Properties | |
|---|---|
| Surface Area (m²/g) | 0.77 |
| Water Absorption (%) | 49.4 |
| Packing Density (kg/m³) | 697.6 |
| alpha alumina content (%) | 98.4 |
| Nitric Acid Leachable, ppmw: | |
| Na | 111 |
| K | 52 |
| Ca | 603 |
| Al | 635 |
| Mg | 85 |
| $SiO_2$ | 1483 |
| Water Leachable K, ppmw | 37 |

Example 3

Testing of the Catalysts

Catalysts A and B were used to produce ethylene oxide from ethylene and oxygen. To do this, 3 to 5 g of the crushed catalyst samples were loaded into separate stainless steel U-shaped tubes. Each tube was immersed in a molten metal bath (heat medium) and the ends were connected to a gas flow system. The weight of catalyst used and the inlet gas flow rate were adjusted to give a gas hourly space velocity of 3300 Nl/(l.h), as calculated for uncrushed catalyst. The inlet gas pressure was 1550 kPa (absolute).

Prior to startup, the catalyst was pre-treated for 3 hours with a gas mixture of 11.4 mole-% oxygen, 7 mole-% carbon dioxide and 81.6 mole-% nitrogen at 280° C. The reactor was then cooled down to 240° C. and a testing gas mixture was introduced. The initial gas mixture passed through the catalyst bed in a "once-through" operation. The gas mixture consisted of 30 volume percent ethylene, 8 volume percent oxygen, 5 volume percent carbon dioxide, 57 volume percent nitrogen and 1.0 to 5.0 parts per million by volume (ppmv) ethyl chloride. For Catalyst A, the initial gas mixture was used for the first 8 days of the test run and the catalyst performance measured. For Catalyst B, the initial gas mixture was used for the first 6 days of the test run and the catalyst performance measured. After this initial testing period, the temperature was changed to 250° C. for 12 hours and the gas mixture was changed to comprise 30 volume percent ethylene, 8 volume percent oxygen, 1 volume percent carbon dioxide, 61 volume percent nitrogen and no ethyl chloride. Ethyl chloride was then introduced into the gas mixture and varied from 1.0 to 5.0 ppmv to obtain maximum selectivity.

During the testing of the catalysts, the temperature was adjusted so as to achieve a constant ethylene oxide content of 3.09 volume percent in the outlet gas stream. The quantity of ethyl chloride was varied to obtain maximum selectivity. The performance data at the 1 mole-% carbon dioxide level was measured between 2 to 3 weeks of operation, once the process equilibrated after the quantity of carbon dioxide in the gas mixture was lowered to 1 mole-%, relative to the total gas mixture. Additional selectivity and temperature values could also be measured over time in order to obtain catalyst stability data. The cesium amounts of the above catalysts are the optimized cesium amounts with respect to the initial selectivity performance of the catalysts.

As shown in Table II, it has been discovered that by depositing silver, a rhenium promoter and additionally, a potassium promoter, on a carrier having a low level of water leachable potassium, an unexpected improvement in catalyst performance is observed when the catalyst is operated under low carbon dioxide conditions during the epoxidation process as compared to the same catalyst without the additional potassium promoter.

TABLE II

| Catalyst | Selectivity (mole-%) at 5 mole-% $CO_2$ | Temperature (° C.) at 5 mole-% $CO_2$ | Selectivity (mole-%) at 1 mole-% $CO_2$ | Temperature (° C.) at 1 mole-% $CO_2$ |
| --- | --- | --- | --- | --- |
| A | 89.5 | 265 | 91.5 | 250 |
| B | 89.9 | 264 | 90.3 | 252 |

Example 4

Catalyst C was prepared using Carrier A and having a final composition of the following, calculated on the basis of pore volume impregnation: 17.5% w silver; 2 mmole Re/kg; 0.6 mmole W/kg; 15 mmole Li/kg; 2 mmole K/kg; and 3.2 mmole Cs/kg. These values are relative to the weight of the catalyst. Ammonium perrhenate, ammonium metatungstate, lithium hydroxide, potassium nitrate and cesium hydroxide were used to prepare Catalyst C.

Catalyst D was prepared using Carrier A and having a final composition of the following, calculated on the basis of pore volume impregnation: 17.5% w silver; 2 mmole Re/kg; 0.6 mmole W/kg; 15 mmole Li/kg; 1 mmole K/kg; and 3.6 mmole Cs/kg. These values are relative to the weight of the catalyst. Ammonium perrhenate, ammonium metatungstate, lithium hydroxide, potassium nitrate and cesium hydroxide were used to prepare Catalyst D.

Catalyst E was prepared using Carrier A and having a final composition of the following, calculated on the basis of pore volume impregnation: 17.5% w silver; 2 mmole Re/kg; 0.6 mmole W/kg; 15 mmole Li/kg; and 4 mmole Cs/kg. These values are relative to the weight of the catalyst. Ammonium perrhenate, ammonium metatungstate, lithium hydroxide, and cesium hydroxide were used to prepare Catalyst E.

Catalysts C, D and E were used to produce ethylene oxide from ethylene and oxygen. To do this, 3 to 5 g of the crushed catalyst samples were loaded into separate stainless steel U-shaped tubes. Each tube was immersed in a molten metal bath (heat medium) and the ends were connected to a gas flow system. The weight of catalyst used and the inlet gas flow rate were adjusted to give a gas hourly space velocity of 3300 Nl/(l.h), as calculated for uncrushed catalyst. The inlet gas pressure was 1550 kPa (absolute).

Prior to startup, the catalyst was pre-treated for 3 hours with a gas mixture of 11.4 mole-% oxygen, 7 mole-% carbon dioxide and 81.6 mole-% nitrogen at 280° C. The reactor was then cooled down to 240° C. and a testing gas mixture was introduced. The initial gas mixture passed through the catalyst bed in a "once-through" operation. The gas mixture consisted of 30 volume percent ethylene, 8 volume percent oxygen, 5 volume percent carbon dioxide, 57 volume percent nitrogen and 1.0 to 5.0 parts per million by volume (ppmv) ethyl chloride which was varied to obtain maximum selectivity. For Catalyst C, the initial gas mixture was used for the first 9 days of the test run and the catalyst performance measured. For Catalyst D, the initial gas mixture was used for the first 7 days of the test run and the catalyst performance measured. For Catalyst E, the initial gas mixture was used for the first 6 days of the test run and the catalyst performance measured. After this initial testing period, the temperature was changed to 250° C. for 12 hours and the gas mixture was changed to comprise 30 volume percent ethylene, 8 volume percent oxygen, 5 volume percent carbon dioxide, 57 volume percent nitrogen and no ethyl chloride. Subsequently, the gas mixture was changed to 30 volume percent ethylene, 8 volume percent oxygen, 1 volume percent carbon dioxide, 61 volume percent nitrogen and from 1.0 to 5.0 ppmv ethyl chloride which was varied to obtain maximum selectivity.

During the testing of the catalysts, the temperature was adjusted so as to achieve a constant ethylene oxide content of 3.09 volume percent in the outlet gas stream. The quantity of ethyl chloride was varied to obtain maximum selectivity. The performance data at the 1 mole-% carbon dioxide level was measured between 2 to 10 days of operation, once the process equilibrated after the quantity of carbon dioxide in the gas mixture was lowered to 1 mole-%, relative to the total gas mixture. Additional selectivity and temperature values could also be measured over time in order to obtain catalyst stability data. The cesium amounts of the above catalysts are the optimized cesium amounts with respect to the initial selectivity performance of the catalysts.

As shown in Table III, it has been discovered that by depositing silver, a rhenium promoter and additionally, a potassium promoter, on a carrier having a low level of water leachable potassium, an unexpected improvement in catalyst performance is observed when the catalyst is operated under low carbon dioxide conditions during the epoxidation process as compared to the same catalyst without the additional potassium promoter.

TABLE III

| Catalyst | Selectivity (mole-%) at 5 mole-% $CO_2$ | Temperature (° C.) at 5 mole-% $CO_2$ | Selectivity (mole-%) at 1 mole-% $CO_2$ | Temperature (° C.) at 1 mole-% $CO_2$ |
| --- | --- | --- | --- | --- |
| C | 88 | 269 | 90.5 | 255 |
| D | 88.8 | 263 | 90 | 249 |
| E | 88.1 | 265 | 88.8 | 252 |

What is claimed is:

1. A process for the epoxidation of an olefin comprising contacting a reactor feed comprising an olefin, oxygen, and carbon dioxide, with a catalyst comprising a carrier and, deposited on the carrier, silver, a rhenium promoter, a potassium promoter, lithium, and cesium; wherein the carbon dioxide is present in the reactor feed in a quantity of at most 3 mole percent based on the total epoxidation reactor feed;

the potassium promoter is deposited on the carrier in a quantity of at least 0.5 mmole/kg, relative to the weight of the catalyst;

the rhenium promoter is deposited on the carrier in a quantity of at least 1.5 mmole/kg, relative to the weight of the catalyst;

lithium and cesium are deposited on the carrier in a combined quantity in the range of from 0.01 to 500 mmole/kg, relative to the weight of the catalyst; and the carrier contains water leachable potassium in a quantity of less than 55 parts per million by weight, relative to the weight of the carrier.

2. The process as claimed in claim 1, wherein the quantity of carbon dioxide is less than 2 mole percent based on the total epoxidation reactor feed.

3. The process as claimed in claim 1, wherein the quantity of carbon dioxide is in the range of from 0.1 to less than 1.5 mole percent based on the total epoxidation reactor feed.

4. The process as claimed in claim 1, wherein the olefin comprises ethylene.

5. The process as claimed in claim 1, wherein the quantity of water leachable potassium in the carrier is at most 50 parts per million by weight, relative to the weight of the carrier.

6. The process as claimed in claim 1, wherein the carrier is a fluoride-mineralized carrier.

7. The process as claimed in claim 1, wherein the quantity of the potassium promoter deposited on the carrier is at least 1 mmole/kg, relative to the weight of the catalyst.

8. The process as claimed in claim 1, wherein the quantity of the potassium promoter deposited on the carrier is in the range of from 1 to 15 mmole/kg, relative to the weight of the catalyst.

9. The process as claimed in claim 1, wherein the catalyst further comprises a further element selected from the group consisting of nitrogen, fluorine, an alkaline earth metal, titanium, hafnium, zirconium, vanadium, thallium, thorium, tantalum, niobium, gallium, germanium, and mixtures thereof.

10. The process as claimed in claim 1, wherein the catalyst contains water extractable potassium in a quantity in the range of from 1.25 to 10 mmole/kg, relative to the weight of the catalyst.

11. The process as claimed in claim 1, wherein the quantity of the rhenium promoter deposited on the carrier is in the range of from 1.5 to 50 mmole/kg, relative to the weight of the catalyst.

12. The process as claimed in claim 1, wherein the catalyst further comprises a rhenium co-promoter selected from the group consisting of tungsten, molybdenum, chromium, sulfur, phosphorous, boron, and mixtures thereof.

13. The process as claimed in claim 1, wherein the catalyst further comprises a first co-promoter selected from sulfur, phosphorus, boron, and mixtures thereof; and a second co-promoter selected from tungsten, molybdenum, chromium, and mixtures thereof.

14. The process as claimed in claim 13, wherein the first co-promoter comprises sulfur.

15. The process as claimed in claim 13, wherein the second co-promoter comprises tungsten.

16. The process as claimed in claim 13, wherein the second co-promoter comprises molybdenum.

17. The process as claimed in claim 13, wherein the molar ratio of the rhenium promoter to the second co-promoter is greater than 1.

18. The process as claimed in claim 13, wherein the first co-promoter is present in a quantity in the range of from 0.2 to 50 mmole/kg, relative to the weight of the catalyst.

19. The process as claimed in claim 13, wherein the second co-promoter is present in a quantity in the range of from 0.1 to 40 mmole/kg, relative to the weight of the catalyst.

20. The process as claimed in claim 1, wherein the combined quantity of lithium and cesium deposited on the carrier is in the range of from 0.5 to 100 mmole/kg, relative to the weight of the catalyst.

21. The process as claimed in claim 13, wherein the first co-promoter is present in a quantity in the range of from 0.2 to 6 mmole/kg, relative to the weight of the catalyst; and the second co-promoter is present in a quantity in the range of from 0.1 to 5 mmole/kg, relative to the weight of the catalyst.

* * * * *